US012756230B2

(12) United States Patent
(10) Patent No.: US 12,756,230 B2
(45) Date of Patent: Oct. 6, 2026

Namdeo et al.

(54) CHARGING AND AMBIENCE MONITORING DEVICE

(71) Applicant: ULTRAHUMAN HEALTHCARE PVT LTD, Bangalore South (IN)

(72) Inventors: Yogansh Namdeo, Bengaluru (IN); Anoop Jayan, Bangalore (IN); Mainak Mitra, West Bengal (IN); Akshay Joshi, Maharashtra (IN); Vishnu Pradeep, Kollam (IN); Gaurav Singh, Gorakhpur (IN); Vinayak MK, Kerala (IN); Mohit Kumar, Bangalore (IN); Bhuvan Srinivasan, Bangalore (IN); Adhit Shet, Bangalore (IN); Vatsal Singhal, Bengaluru (IN)

(73) Assignee: ULTRAHUMAN HEALTHCARE PVT LTD, Bangalore South (IN)

( * ) Notice: Subject to any disclaimer, the term of this patent is extended or adjusted under 35 U.S.C. 154(b) by 0 days.

(21) Appl. No.: 19/035,482

(22) Filed: Jan. 23, 2025

(65) Prior Publication Data

US 2025/0279677 A1 Sep. 4, 2025

(30) Foreign Application Priority Data

Jan. 23, 2024 (IN) ............................. 202341079621

(51) Int. Cl.

| | |
|---|---|
| ***H02J 50/00*** | (2016.01) |
| ***G01D 1/18*** | (2006.01) |
| ***G01J 1/42*** | (2006.01) |
| ***G06F 1/16*** | (2006.01) |
| ***H02J 50/10*** | (2016.01) |
| ***H02J 50/90*** | (2016.01) |
| *A61B 5/00* | (2006.01) |

(52) U.S. Cl.

CPC .............. *H02J 50/005* (2020.01); *G01D 1/18* (2013.01); *G01J 1/4204* (2013.01); *G06F 1/163* (2013.01); *H02J 50/10* (2016.02); *H02J 50/90* (2016.02); *A61B 5/4812* (2013.01); *A61B 2560/0242* (2013.01)

(58) Field of Classification Search

CPC ........ H02J 50/005; H02J 50/90; A61B 5/4812

USPC ........................................................... 307/11

See application file for complete search history.

(56) References Cited

U.S. PATENT DOCUMENTS 6,711,414 B1 * 3/2004 Lightman .............. G06Q 30/02 455/457
8,928,182 B2 * 1/2015 Kurata .................... H02J 50/12 307/104
9,836,069 B1 * 12/2017 Nelmes .................. G05B 15/02
9,947,184 B2 * 4/2018 Robinson ................ G08B 5/22

(Continued)

*Primary Examiner* — Alfonso Perez Borroto

(74) *Attorney, Agent, or Firm* — Renner, Otto, Boisselle & Sklar, LLP

(57) ABSTRACT

The proposed invention relates to a charging device. The charging device comprises a plurality of sensors configured to monitor different environmental conditions and user activity. Additionally, the charging device includes a controller connected with the plurality of sensors. The controller is configured to process data received from the plurality of sensors. A wireless communication module is connected with the controller to transmit processed data to a server. The server processes the sensor data and user activity data and send instructions to the charging device for operating one or more IoT devices connected with the charging device.

18 Claims, 3 Drawing Sheets

(56) References Cited

U.S. PATENT DOCUMENTS

2013/0099586 A1* 4/2013 Kato .................... H02J 50/005
307/104
2015/0200549 A1* 7/2015 Michisaka ............. H02J 7/933
307/31
2016/0042630 A1* 2/2016 Cho ....................... G08B 19/00
340/517
2016/0165409 A1* 6/2016 Bulut ...................... H04W 4/06
715/734
2016/0224126 A1* 8/2016 Andersson ................ G06F 3/03
2021/0121136 A1* 4/2021 Dobson .................. A61B 5/002
2021/0186342 A1* 6/2021 Bogdanovich ....... A61B 5/0022
2022/0141196 A1* 5/2022 Kwatra ............... H04L 63/0421
726/26
2022/0209581 A1* 6/2022 Kim ........................ H02J 50/10
2023/0210395 A1* 7/2023 Singleton ................. A61B 5/01
600/504

* cited by examiner

CHARGING AND AMBIENCE MONITORING DEVICE

FIELD OF INVENTION

This application claims priority to Indian Application No. 202341079621, filed Jan. 23, 2024, which is hereby incorporated herein by reference in its entirety.

BACKGROUND

An individual/user is exposed to varying levels of environmental conditions in a closed space, such as home or office. The environmental conditions include factors such as varying levels of light, noise, air quality, and radiations. Such environmental conditions highly impact day-to-day life and wellness of the user. However, regular health and fitness monitoring devices, especially smart wearable devices only considers bodily parameters and physiological data of the user.

With advancement in technology, the user is surrounded by smart or electronic devices in his home or office. While on one hand the smart or electronic devices ease life of the user, on another hand the smart or electronic devices create newer problems and distractions for the user, such as disturbance in sleep, emission of high intensity light, and electromagnetic radiations. Over exposure or ill-timed usage of the smart or electronic devices have contributed to deteriorating wellness of the user.

Thus, there is a need of a system that monitors wellness of the user based on ambient conditions and also automatically controls the ambient conditions for ensuring wellness of the user.

OBJECTS OF THE INVENTION

A general objective of the present invention is to offer an automatic wellness solution to the user.

Another objective of the invention is to provide a portable charging and ambience monitoring device.

Yet another objective of the invention is to determine overall wellness of the user based on physiological and environmental conditions of a user.

Still another objective of the invention is to automatically control ambient conditions of the user to promote wellness.

SUMMARY OF THE INVENTION

The present invention relates to a charging device. The charging device may comprise a Printed Circuit Board (PCB). A plurality of sensors may be mounted on the PCB. The plurality of sensors may include sound level sensors, photodetectors, air quality sensors, and Radio Frequency meters, for monitoring ambient conditions of a user.

In one aspect, charging device may comprise wireless charging circuitry for wireless charging of an smart wearable device, such as an electronic ring.

In one aspect, the charging device may be configured to communicate with a server for providing one or more sensor data captured by the plurality of sensors.

In one aspect, the server may analyse impact of ambient conditions monitored by the charging device and physiological conditions of the user monitored by the smart wearable device, on an overall lifestyle of the user.

In one aspect, the charging device may control Internet of Things (IoT) devices connected to the charging device for ensuring wellness of the user, based on the analysis received from the server.

In one aspect, the server may determine circadian rhythm of the user based on intensity of light the user is exposed to during a 24-hour cycle.

In one aspect, the charging device may determine sleep quality of the user based on snoring sounds of the user.

In an embodiment of the present disclosure, a charging device comprises a plurality of sensors configured to monitor different environmental conditions and user activity. A controller connected with the plurality of sensors. The controller is configured to process data received from the plurality of sensors and a wireless communication module connected with the controller to transmit processed data to a server.

In an aspect of the present disclosure, the plurality of sensors includes a sound sensor, a photodetector, a humidity sensor, a temperature sensor, an air quality sensor, and a radio frequency meter.

In another aspect of the present disclosure, the charging device further comprises an infrared camera connected with the controller to monitor the user activity.

In another aspect of the present disclosure, the wireless communication module operates using Bluetooth, Wi-Fi, or Near Field Communication (NFC).

In another aspect of the present disclosure, the charging device further comprises a wireless charging coil for wireless charging of a smart wearable device.

In another aspect of the present disclosure, the charging device further comprises a speaker for providing notifications and alerts to the user.

In another aspect of the present disclosure, the charging device further communicates with other charging devices present in vicinity, for communicating the data to server.

In another aspect of the present disclosure, the charging device further comprises a power source to power the plurality of sensors, the controller and the wireless module.

In another embodiment of the present disclosure, a server for managing ambient conditions of a user comprises a processor configured to execute instructions for operating one or more IoT devices connected with the charging device. Additionally, the server includes a memory coupled to the processor configured to stores a program readable by the processor for executing a method of operating one or more IoT devices connected with the charging device includes receiving sensor data and user activity data from one of a smart wearable device and the charging device. The server receives user preferences from a user device and sends instructions to the charging device for operating one or more IoT devices connected with the charging device. The instructions are sent based on the sensor data and the user preferences. Furthermore, the server receives information of usage pattern of the IoT devices by the user. The server provides recommendations to the user for storing the information as the user preferences, and sends the instructions, based on a response of the user, to the charging device for operating the one or more IoT devices.

In another aspect of the present disclosure, the recommendations are provided to the user and the user preferences are received from the user through a user device.

In another aspect of the present disclosure, wherein the user device includes a smartphone, tablet, or a laptop.

Other aspects and advantages of the invention will become apparent from the following description, taken in conjunction with the accompanying drawings, illustrating by way of example the principles of the invention.

BRIEF DESCRIPTION OF THE DRAWINGS

The accompanying drawings constitute a part of the description and are used to provide further understanding of the present invention. Such accompanying drawings illustrate the embodiments of the present invention which are used to describe the principles of the present invention. The embodiments are illustrated by way of example and not by way of limitation in the figures of the accompanying drawings in which like references indicate similar elements. It should be noted that references to “an” or “one” embodiment in this invention are not necessarily to the same embodiment, and they mean at least one. In the drawings.

DETAILED DESCRIPTION OF THE INVENTION

The detailed description set forth below in connection with the appended drawings is intended as a description of various embodiments of the present invention and is not intended to represent the only embodiments in which the present invention may be practiced. Each embodiment described in this disclosure is provided merely as an example or illustration of the present invention, and should not necessarily be construed as preferred or advantageous over other embodiments. The detailed description includes specific details for the purpose of providing a thorough understanding of the present invention. However, it will be apparent to those skilled in the art that the present invention may be practiced without these specific details.

The proposed invention relates to a charging device. The charging device may be a charging apparatus for charging smart wearable devices of a user, especially an electronic ring. The charging device may be configured to collect and monitor data related to ambience of a user, and may also control Internet of Things (IoT) devices in surroundings of the user. The charging device may further be configured to process and store data related to the ambience of the user and also operate with data collected by the wearable device, to provide feedback to the user related to impact of various aspects of ambience of the user. The charging device may also control the IoT devices to control various aspects of ambience of the user for promoting user’s wellness.

Figure 1:
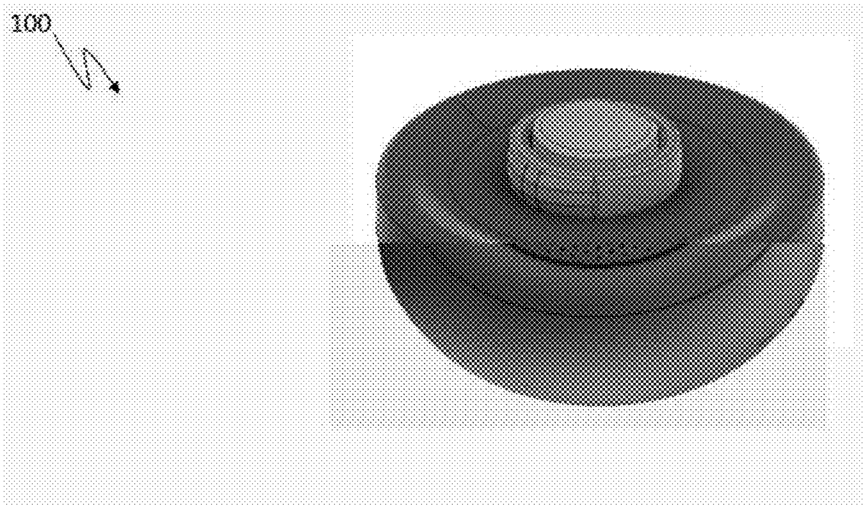
FIG. 1 illustrates a charging and ambience monitoring device, in accordance with an embodiment of the present invention.

The charging device may be configured to charge an smart wearable device, and also be configured to monitor conditions in ambience of the user, for assessing impact of ambience of user on his lifestyle. FIG. 1 illustrates a charging and ambience monitoring device, in accordance with an embodiment of the present invention. The charging device 100 may be designed in shape of a spherical or tubular pod and configured to rest horizontally on a surface. The charging device 100 may comprise a Printed Circuit Board (PCB) 218. The PCB 218 may comprise any type of PCB, including but not limited to a single sided PCB, double sided PCB, multi layered PCB, and/or a flexible PCB. The PCB 218 may include a plurality of sensors 202 (collectively referred to as sensors) and a controller 204 configured to interact with the plurality of sensors 202. The controller 204 may be configured to couple with a memory of its own or a memory separately mounted on the PCB 218, for storing data acquired from the sensors.

In one implementation, the plurality of sensors 202 may include one or more sound level sensors for measuring intensity of noise in surroundings of the charging device 100. The one or more sound level sensors may measure noise with an accuracy of 3 dB (decibel) in a range of 30 dB to 110 dB. The sound level sensors may also be useful in monitoring snoring sounds of the user when he is asleep. The plurality of sensors 202 may also include one or more photodetectors for monitoring intensity of light in the surroundings of the charging device 100. The photodetectors may measure illuminance by converting light energy to electrical signals. The photodetectors respond to changes in the amount of light received, and may monitor the intensity of light during various times of the day.

The charging device 100 may also be configured to measure various environmental conditions in the ambience of the user, such as humidity, temperature, air quality, and/or other allergens in the air by utilising humidity sensors, temperature sensors, and air-quality sensors. The air-quality sensors may monitor presence of organic compounds, particulate matters and other air-borne impurities in surroundings of the charging device 100. The air quality sensors may capture deterioration in quality of air in the ambience, due to factors such as indoor air pollution or smoking habits of the user. The charging device 100 may further utilise Radio Frequency (RF) meters for measurement of electromagnetic radiations that a user may be exposed to. The RF meter may measure the electromagnetic radiations emitted from various electronic devices in the vicinity of the user, such as mobile phones and wireless communication towers.

For scanning overall environment of the user, the controller 204 may further be connected with an Infrared (IR) camera 208 provided in the charging device 100. The IR camera 208 may capture values of movement of the user. The controller 204 may also be connected to a microphone 212 and a speaker 214. The microphone 212 may enable the charging device 100 to receive voice commands of the user. The speaker 214 may be utilised for playing wellness music for the user and also to provide alarms and alert to the user.

The charging device 100 may be connected with a server and/or one or more IoT devices through a radio based wireless module 206. The wireless module 206 may work on one or more of Bluetooth, Wi-Fi, Near Field Communication (NFC). The wireless module 206 may be mounted on the PCB 218 to wirelessly communicate plurality of physiological data and environmental data to a server. The wireless module 206 may also enable the controller 204 to communicate with the IoT devices. The charging device 100 may further comprise a power source 216 such as a battery for powering the plurality of sensors 202, the controller 204, and the radio based wireless module 206. The charging device 100 may further comprise a port/connector to receive power, for example a Universal Serial Bus (USB) port.

The charging device 100 may further be configured to hold a smart wearable device. In one embodiment the smart wearable device may be an electronic ring of a particular size, for charging. The charging device 100 may comprise a circuitry for wireless charging of the electronic ring. For wireless charging, the charging device 100 may comprise a wireless charging coil 210 present on a surface of the device. Electromagnetic field generated by the wireless charging coil 210 may get coupled with a coil of the electronic ring when the electronic ring is present in contact with the surface. Through coupling of the electromagnetic field, power from the charging device 100 may be received and stored in the battery of the electronic ring. The charging device 100 may also comprise a power converter for converting Alternating Current (AC) wall voltage may be converted to a Direct Current (DC) for supply of the DC current to the wireless charging coil 210.

Figure 2:
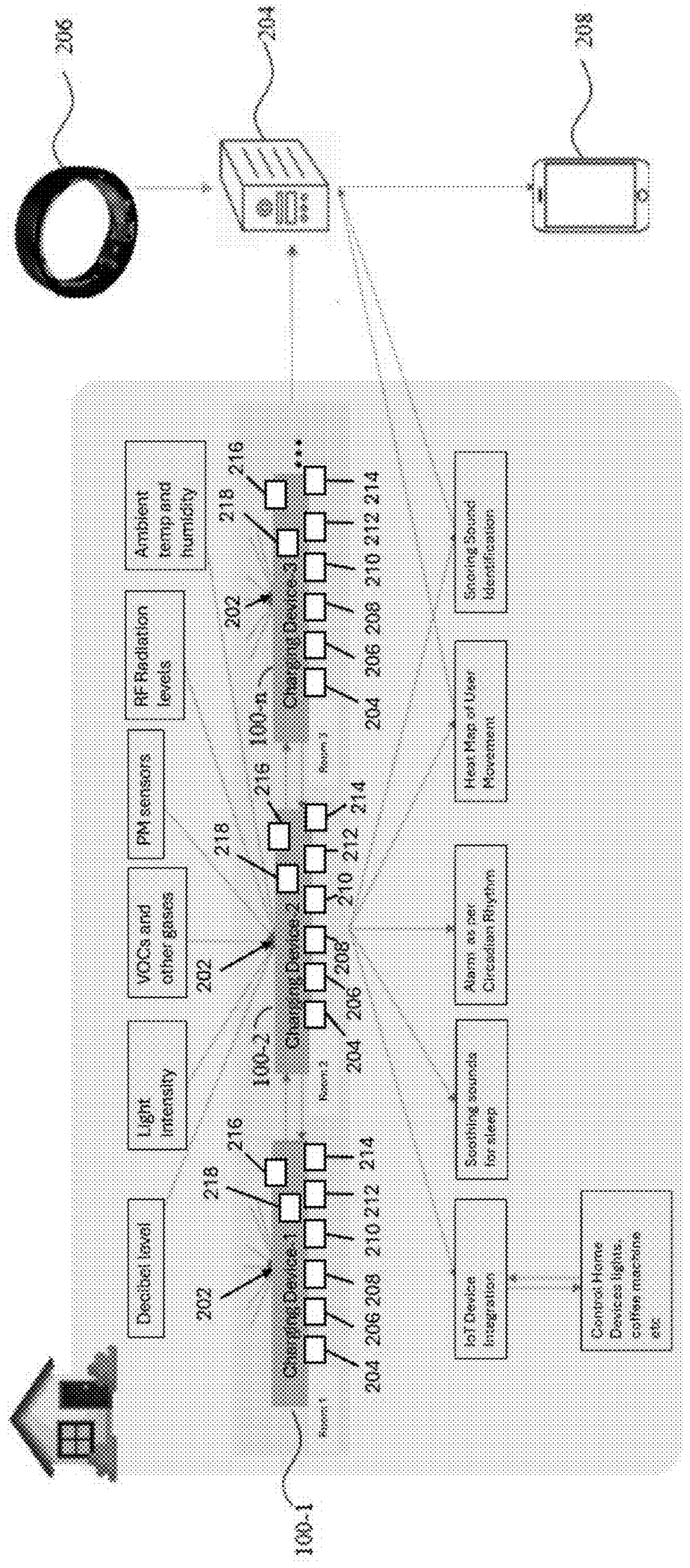
FIG. 2 illustrates a system for monitoring ambient conditions of a user, in accordance with an embodiment of the present invention.

FIG. 2 illustrates a system for monitoring ambient conditions of a user, in accordance with an embodiment of the present invention. The system may include one or more charging device 100-1 to 100-*n* (collectively referred to as charging device 100) connected to each other via wireless network. The charging device 100 may further be coupled to a server 204. The server 204 may be hosted locally or over a cloud network. The charging device 100 may transmit ambient data (alternatively referred to as one or more sensor data) captured from the plurality of sensors 202. The server 204 may also receive physiological data of the user monitored using the smart wearable device 206. The physiological data may include user data related to sleep patterns of the user, motion, and heart rate variability of the user through wireless network. The server 204 may run programmed instructions for processing the one or more sensor data and carrying out an algorithm for analysing impact of ambient conditions on lifestyle of the user, based on the one or more sensor data and the user data. The server 204 may further be configured to interact with a user device 208 through the wireless network. The user device 208 may be a processing device, such as a smartphone, tablet, or a laptop configured to run an application or software. The application or software may be used to display one or more of the sensor data, the user data, and the impact of the ambient conditions on the user. The server 204 may provide details of analysis of the ambient conditions to the user as a feedback to the user, to enable him to monitor his lifestyle. Based on the details of analysis of the ambient conditions, the server 204 may communicate with the charging device 100 to automatically control IoT devices connected to the charging device 100 for ensuring optimum health and wellness of the user.

In one implementation, the server 204 may utilise one or more sensor data such as user movement, light intensity levels, temperature, and humidity for determining circadian rhythm of the user based on the ambient conditions. The circadian rhythm may include physical, mental, and behavioural changes in the user in a 24-hour cycle in response to exposure to varying light intensities and noises around the user. Based on the circadian rhythm, an alarm may automatically be set on the charging device 100 for the user. The circadian rhythm may also be used for assessing health conditions of the user.

In another implementation, the server 204 may utilise values of noise levels in surroundings of the user for identifying snoring sound of the user. The server 204 may filter out snoring sounds of the user by reducing background noises of the user. Additionally, the server 204 may also utilise respiratory flow rate captured by the smart wearable device, to determine an extent to which snoring is present. Based on a snoring of the user, the server 204 may determine sleep patterns of the user and may calculate quality of sleep of the user, and an amount of time the user was in light sleep and deep sleep conditions. Based on the sleep patterns of the user, the charging device 100 may play soothing music at night to help the user to fall asleep.

In another implementation, based on user preference and sleep patterns of the user, determined by the server 204, the server 204 may further determine a time slot during a day of the user where the user may consume caffeine so as to not impact his sleep. The charging device 100 may command a coffee machine connected to it wirelessly, to produce coffee in the morning and disable the coffee machine post afternoon to ensure a good sleep for the user at night. In another scenario, the charging device 100 may also turn off an IoT connected light when one of the smart wearable device 206 or the charging device 100 may detect that the user has fallen asleep and turn it on when the user wakes up.

In another implementation, the server 204 may determine impact of the ambient conditions on lifestyle of the user and may control IoT devices via the charging device 100 for ensuring wellness of the user. The server 204 may also provide guidance to the user on the user device 208 to improve their sleep hygiene in order to improve overall wellness and sleep quality. For an example, if the user is determined to be a smoker and local air quality sensors detects a decrease in air quality, an alert may be provided to the user not to smoke. Alternatively, the server 204 may instruct the charging device 100 to turn on an IoT enabled air purifier.

In yet another implementation, one or more charging device 100-1 to 100-*n* may create a wireless mesh among themselves and track position of the smart wearable device at all times in premises of the user, to form a heat map of the user's movements and holistically determined overall ambient conditions that the user is exposed to. The user may receive suggestions on the user device 208 as to which charging device 100 offers best environment for different functions during the day and for good sleep at night.

Figure 3:
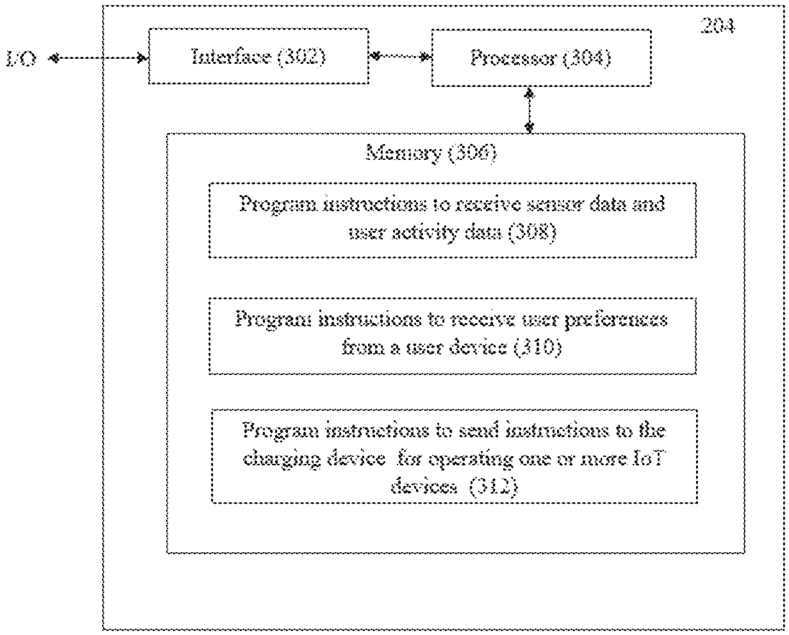
FIG. 3 illustrates a block diagram of the server for managing ambient conditions of a user, in accordance with an embodiment of the present invention.

FIG. 3 illustrates a block diagram of the server 204 for managing ambient conditions of a user, in accordance with an embodiment of the present invention. The server 204 may comprise one or more network interfaces 302 (e.g., wired, wireless, etc.), at least one processor 304, and a memory 306. The one or more network interfaces 302 may be used to provide input or fetch output from the server 204. The one or more network interfaces 302 may be implemented as a Command Line Interface (CLI) or a Graphical User Interface (GUI). Further, Application Programming Interfaces (APIs) may also be used for remotely interacting with edge systems and cloud servers.

The processor 304 may include one or more general purpose processors (e.g., INTEL® or Advanced Micro Devices® (AMD) microprocessors) and/or one or more special purpose processors (e.g., digital signal processors or Xilinx® System on Chip (SOC) Field Programmable Gate Array (FPGA) processor), MIPS/ARM-class processor, a microprocessor, a digital signal processor, an application specific integrated circuit, a microcontroller, a state machine, or any type of programmable logic array.

The memory 306 of the server 204 may store program instructions for managing ambient conditions of a user. Functional code stored in the memory 306 may include program instructions to determine to receive sensor data and user activity data 308, program instructions to receive user preferences from a user device 310, and program instructions to send instructions to the charging device for operating one or more IoT devices 312.

The program instructions to determine to receive sensor data and user activity data 308 cause the processor to receives sensor data and user activity data from either a smart wearable device 204 or the charging device 100. The program instructions to receive user preferences from a user device 310 cause the processor to receive the user preference from the user device 208 through a software or any application. Further, the program instructions to send instructions to the charging device for operating one or more IoT devices 312 cause the processor to sends instructions to the charging device 100 to control the connected IoT devices based on the sensor data and user preferences. Furthermore, the server 204 is configured to receive information regarding the usage patterns of the IoT devices through the charging device 100 and provide recommendations to the user for storing the usage pattern information as user preferences. The server 204 then sends the necessary instructions to the charging device 100 for operating the one or more IoT devices based on these preferences.

In one implementation the charging device 100 is configured to control an Air Conditioning (AC) unit by setting it to 27 degree Celsius at 10:00 PM every day. The instructions for this operation are provided by the user through a user device 208 such as a smartphone, where an application or software installed on the user device 208 allows the user to input their preferences. Such preferences are transmitted to the server 204. Further the server 204 processes the instructions and stores the information in its memory 306. At the specified time (i.e. at 10 pm every day), the server sends a command to the charging device 100 to switch ON the AC unit at the desired temperature (27 degree Celsius) based on the preference of user.

In another implementation, the server 204 receives information about the usage pattern of the coffee machine through the charging device 100 by the user, identifying that the user operates the coffee machine at 8:00 AM every day. Based on this pattern, the server 204 provides recommendations to the user through the user device 208 for storing this routine as a user preference by asking would you like to add command "Turning ON the coffee machine at 8:00 AM" to the preference list". Once the user confirms or accepts the recommendation via an application or software on the user device 208, the server 204 stores the preference in its memory 306. Further, the server 204 sends instructions to the charging device 100 to automatically operate the coffee machine at 8:00 AM every day, ensuring a seamless and efficient experience without requiring manual intervention from the user.

The present invention offers a dynamic solution to the user for controlling his wellness. The present invention tracks the user's wellness not only on basis of user's bodily parameters but also on basis of the environment the user is exposed to. The present invention analysis the effect of user's bodily parameters and his environmental conditions and helps him improve his wellness.

In the above detailed description, reference is made to the accompanying drawings that form a part thereof, and illustrate the best mode presently contemplated for carrying out the invention. However, such description should not be considered as any limitation of scope of the present unit. The structure thus conceived in the present description is susceptible of numerous modifications and variations, all the details may furthermore be replaced with elements having technical equivalence.

We claim:

1. A charging device, comprising:
- a plurality of sensors configured to monitor different environmental conditions and user activity;
- a controller connected with the plurality of sensors, wherein the controller is configured to process data received from the plurality of sensors;
- a wireless communication module connected with the controller to transmit processed data to a server; and
- a wireless charging coil configured to perform wireless charging of a smart wearable device,
  - wherein the controller is programmed to analyze environmental data over time to determine user-specific circadian rhythm patterns based on variations in light exposure and noise levels, and
  - wherein the charging device is configured to generate an alarm based on the determined user-specific circadian rhythm of the user.

2. The charging device as claimed in claim 1, wherein the plurality of sensors includes a sound sensor, a photodetector, a humidity sensor, a temperature sensor, an air quality sensor, and a radio frequency meter.

3. The charging device as claimed in claim 1, further comprises an infrared camera connected with the controller to monitor the user activity.

4. The charging device as claimed in claim 1, wherein the wireless communication module operates using Bluetooth, Wi-Fi, Near Field Communication (NFC).

5. The charging device as claimed in claim 1, further comprises a microphone for receiving voice commands of the user.

6. The charging device as claimed in claim 1, further comprises a speaker for providing notifications and alerts to the user.

7. The charging device as claimed in claim 1, further communicates with other charging devices present in vicinity, for communicating the data to server.

8. The charging device as claimed in claim 1, further receives user preferences from the server, and communicates with IoT devices for implementing the user preference.

9. The charging device as claimed in claim 1, further comprises a power source to power the plurality of sensors, the controller and the wireless module.

10. The charging device as claimed in claim 1, comprising a Printed Circuit Board (PCB) integrated with one or more layers selected from single-sided, double-sided, or multi-layered configurations, for integrating the plurality of sensors and the controller to facilitate data collection and processing.

11. The charging device as claimed in claim 1, wherein the wireless charging coil is mounted on a surface of the charging device and configured to generate an electromagnetic field for inductive charging of the wearable device, wherein power is transferred when the wearable device is in contact with or proximate to the wireless charging coil.

12. The charging device as claimed in claim 1, wherein the wireless charging coil is further configured to adjust the electromagnetic field strength based on the proximity of the wearable device to optimize power transfer efficiency.

13. The charging device as claimed in claim 10, wherein the Printed Circuit Board (PCB) includes connections to the wireless communication module, enabling transmission of data captured by the plurality of sensors to a server.

14. The charging device as claimed in claim 10, wherein the Printed Circuit Board (PCB) includes a power converter configured to convert alternating current (AC) from an external power source to direct current (DC) for powering the plurality of sensors, the controller, and the wireless communication module.

15. The charging device as claimed in claim 1, wherein the charging device may be controlled by a server for controlling IoT devices for ensuring optimum health and wellness of the user.

16. A server for managing ambient conditions of a user, comprises:
- a processor;
- a memory coupled to the processor configured to store a program readable by the processor to:
- receive sensor data and user activity data from one of a smart wearable device (204) and a charging device;
- receive user preferences defining operation of IoT devices from a user device; and send instructions to the charging device for operating one or more IoT devices connected with the charging device, wherein the instructions are sent based on the sensor data and the user preference.

17. The server as claimed in claim 16, wherein the server:

receives, through the charging device, information of usage pattern of the one or more IoT devices by the user;

provides recommendations to the user for storing the information as the user preferences; and sends the instructions to the charging device for operating the one or more IoT devices based on a response of the user towards the recommendations.

18. The server as claimed in claim 16, wherein the recommendations are provided to the user and the user preferences are received from the user through a user device.

* * * * *